(12) United States Patent
van Agthoven et al.

(10) Patent No.: US 7,300,797 B2
(45) Date of Patent: Nov. 27, 2007

(54) LYSIS REAGENT FOR BLOOD CELL ANALYSIS

(75) Inventors: Andre van Agthoven, Marseilles (FR); Jean-Pierre Daziano, Marseilles (FR); John Allen Maples, Miami, FL (US)

(73) Assignee: Immunotech, S.A., Marseilles (FR)

( * ) Notice: Subject to any disclaimer, the term of this patent is extended or adjusted under 35 U.S.C. 154(b) by 176 days.

(21) Appl. No.: 09/951,903

(22) Filed: Sep. 14, 2001

(65) Prior Publication Data

US 2002/0115118 A1    Aug. 22, 2002

(30) Foreign Application Priority Data

Sep. 14, 2000    (FR) ................................. 00 11746

(51) Int. Cl.
*G01N 31/00*    (2006.01)

(52) U.S. Cl. .................. 436/17; 356/73; 356/317; 356/336; 356/39; 516/77

(58) Field of Classification Search ................ 356/39, 356/73, 317, 336; 435/2, 7.1–7.25, 10, 17, 435/269; 436/10, 17, 65; 516/77
See application file for complete search history.

(56) References Cited

U.S. PATENT DOCUMENTS

| | | | |
|---|---|---|---|
| 4,710,573 A * | 12/1987 | Strupczewski | 546/199 |
| 5,116,539 A * | 5/1992 | Hamaguchi et al. | 516/77 |
| 5,389,549 A * | 2/1995 | Hamaguchi et al. | 436/10 |
| 5,516,695 A * | 5/1996 | Kim et al. | 436/17 |
| 5,559,037 A * | 9/1996 | Kim et al. | 436/63 |
| 5,605,579 A * | 2/1997 | Distaso | 134/38 |
| 5,686,308 A * | 11/1997 | Li et al. | 436/63 |
| 5,721,236 A * | 2/1998 | Bishop et al. | 514/253.03 |
| 5,843,608 A * | 12/1998 | Li et al. | 436/63 |
| 5,882,933 A * | 3/1999 | Li et al. | 436/63 |
| 5,917,584 A * | 6/1999 | Li et al. | 356/39 |
| 6,489,300 B1 * | 12/2002 | Thorsett et al. | 514/19 |
| 2003/0040115 A1* | 2/2003 | Li et al. | 436/17 |

FOREIGN PATENT DOCUMENTS

WO    WO 92/00961    *    1/1992

OTHER PUBLICATIONS

Chen et al, Death signaling pathway induced by pyrrolidine dithiocarbamate-Cu2+ complex in the cultured rat cortical astrocytes, 200, GLIA, 31:249-261.*

(Continued)

*Primary Examiner*—Long V. Le
*Assistant Examiner*—N Yang
(74) *Attorney, Agent, or Firm*—Cuspa Technology Law Associates; Mitchell E. Alter

(57) ABSTRACT

A multifunctional reagent for erythrocytes containing an amount sufficient to produce the lysis of erythrocytes or the sphering of erythrocytes in such a way that they can be detected by a cytometer or an automatic counting device, of a carbamate or of an agent inducing the formation by the erythrocytes, from carbonate and from a nitrogenated heterocycle or ammonium ions, of a carbamate combined with the absorption of $CO_2$ by said erythrocytes, process for lysing or sphering erythrocytes and preparation process for leucocytes.

28 Claims, 2 Drawing Sheets

OTHER PUBLICATIONS

Figure 1:
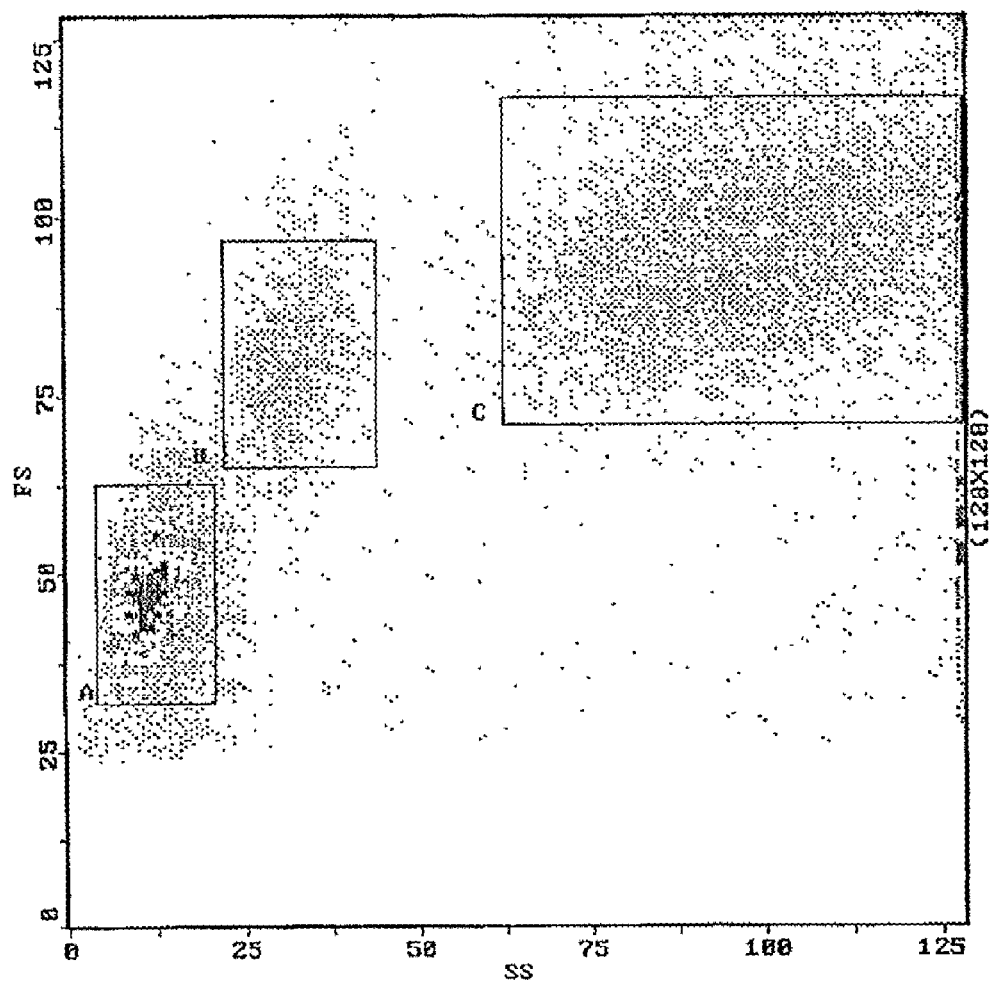

Wilson et al, Toxicologic effects of ammonium carbamate and related compounds, 1968, Am J Vet Res, 29 (4), p. 897-906.*

Konialis et al, Cloned cDNA for rabbit erythrocyte carbonic anhydrase I: a novel erythrocyte specific probe to study development in erythroid tissues, 1985, Proc Natl Acad Sci USA, 82, 663-667.*

Tu et al, Inhibition by cupric ions of 18O exchange catalyzed by human carbonic anhydrase II, 1981, J Biol Chem, 266(18), 9466-9470.*

Henderson et al, Synthesis and anti-cancer activity of 2,6-disubstituted N-methylpiperidine derivatives and their N-oxides, 1996, Anti-Cancer Drug Design, 11, 421-438.*

Murakami et al, Purification and characterization of human salivary carbonic anhydrase, 1987, J Bio Chem, 262(3), 1382-1388.*

Porter et al, CO2 adducts as reactive analogues of carboxylate substrates for aconitase and other enzymes of carbohydrate metabolism, 1987, J Bio Chem, 262(14), 6552-6563.*

Jespersen, A thermochemical study of the hydrolysis of urea by urease, 1975, J Am Chem Soc, 97:7, 1662-1667.*

S.H. Boyer et al.: "Enrichment of erythrocytes of fetal origin from adult-fetal blood mixtures via selective hemolysis of adult blood cells: an aid to antenatal diagnosis of hemoglobinpathies." BLOOD, vol. 47, No. 6 Jun. 1976 pp. 883-897.

* cited by examiner

LYSIS REAGENT FOR BLOOD CELL ANALYSIS

The present invention relates to new reagents and methods for the treatment, and in particular the lysis of erythrocytes.

Red corpuscles are approximately one thousand times more numerous than leucocytes, they form a barrier to the analysis of the leucocytic fraction of the blood. Treatment of blood with a lysis reagent empties the red blood cells of their contents and makes it possible to isolate these cells from the analysis. An ideal lysis process comprises complete lysis of all the erythrocytic elements, without the slightest effect on the morphology and the viability of the leucocytes.

Hypotonic lyses are known among the numerous lysis reagents and methods. But a deformation of the leucocytes is observed.

Detergents are also known, but these produce a deterioration in the membrane of the leucocytes which are therefore counted by default.

Small neutral, generally lipophilic molecules are also used such as alcohols or aldehydes but these have the drawback of being toxic for the leucocytes.

In fact, reagents containing amines have performance values closer to an ideal lysis process. The lysis reagents containing amines include the ammonium chloride reagent, the use of which is very widespread and the reagent based on nitrogenated heterocycles, as described in FR-A-2 778 413. Lysis reagents with ammonium chloride contain 155 mM $NH_4Cl$, 10 mM $KHCO_3$ and can sometimes also contain 0.1 mM EDTA.

However, as described in FR-A-2 778 413, as the ammonium chloride lysis reagent has a rapid and complete lysis effect, it has a toxic effect on the leucocytes. The problem of the non-specific toxicity of ammonium chloride is probably linked to the presence of an ammonia concentration of approximately 1 mM in the lysis mixture. The use of stronger bases, such as pyrrolidine and piperidine with a free base concentration of approximately 10 µM, resolves the problem of non-specific toxicity, but gives a slower lysis reaction, this which is a drawback for its use in routine laboratories.

It would therefore be desirable to have available new reagents and lysis methods for erythrocytes with a more rapid and more complete action.

After much research the Applicant has surprisingly discovered that lysis reagents, and in particular reagents containing amines in the presence of a carbamate and/or of a catalyst of the reaction $$CO_2 + H_2O \leftrightarrows H_2CO_3$$

or/and of the reaction $$carbonate \leftrightarrows carbamate + H_2O$$

which are the two reactions involved in the formation of carbamate during the absorption of $CO_2$ by the erythrocyte, brought about a more rapid and more complete lysis of the erythrocytes than in the absence of these reagents.

The influence of the presence of a carbamate in a lysis reagent on the speed of lysis is shown below in the experimental part.

That is why a subject of the present application is a multifunctional reagent for erythrocytes characterized in that it contains a quantity sufficient to produce the lysis or the sphering of the erythrocytes so that they can be detected and counted by a cytometer or an automatic counting device, Of a carbamate of a nitrogenated heterocycle or of a halide such as ammonium chloride or Of an agent inducing the formation by the erythrocytes, from carbonate and a nitrogenated heterocycle or ammonium ions, of a carbamate combined with the absorption of $CO_2$ by said erythrocytes.

The multifunctional reagent according to the invention permits either effective lysis of the erythrocytes or if desired the production of their simple sphering.

In preferential conditions for the implementation of the invention, the carbamate can be used in the molar concentration of 0.000001 M to 0.1 M, particularly 0.00001 M to 0.01 M and quite particularly 0.0001 M to 0.005 M. In wholly preferential conditions for the implementation of the lysis reagent described above, a concentration of 0.0004 M is used.

In other preferential conditions for the implementation of the invention, the agent inducing the formation by the erythrocytes, from carbonate or an amine base, of a carbamate combined with the absorption of $CO_2$ by said erythrocytes, is a catalyst agent of the reaction $$CO_2 + H_2O \leftrightarrows H_2CO_3$$

such as carbonic anhydrase, for example carbonic anhydrase I or carbonic anhydrase II. The enzyme can have varied isoelectric points and can have various sources as their origin. The activity of the enzyme is expressed in Wilbur-Anderson units. The carbonic anhydrase can be present in the concentration of 1 W-A U/liter to 1,000,000 W-A U/liter, particularly from 10 W-A U/liter to 500,000 W-A U/liter and very particularly from 100 W-A U/liter to 100,000 W-A U/liter. In wholly preferential conditions for the implementation of the lysis reagent described above, a concentration of approximately 50,000 W-A U/liter is used.

In the present application and in the following, the nitrogenated heterocycle in part constituting the carbamate can be for example bicylic and preferably monocyclic. It can be unsaturated and in this case comprises for example 5, preferably 4, in particular 3, particularly 2 double bonds, and it is preferably saturated. It comprises for example from 3 to 8, in particular from 3 to 6 and particularly from 3 to 5, and very particularly 4 or 5 carbon atoms. It comprises 2, in particular 1 single nitrogen atom.

As saturated nitrogenated heterocycle there can for example be mentioned pyrazolidine, imidazolidine, the imidazoline and piperazine, in particular morpholine and particularly piperidine or pyrrolidine.

In other preferential conditions for the implementation of the invention, the multifunctional reagent for erythrocytes moreover contains a nitrogenated heterocycle or an ammonium salt such as a halide like chloride.

The nitrogenated heterocycle can be one of those previously mentioned.

In a multifunctional reagent according to the invention, the nitrogenated heterocycle can be present in the molar concentration of 0.01 to 0.250 M, particularly 0.08 to 0.19 M and very particularly 0.12 to 0.18 M. In wholly preferential conditions for the implementation of the multifunctional reagent described above, a concentration of 0.17 M is used.

The concentrations of the compound concerned in the reaction medium (multifunctional reagent+blood sample) during erythrocytic lysis are preferably 0.01 to 0.225 M, particularly 0.072 to 0.17 M and very particularly 0.11 to 0.17 M.

In a multifunctional reagent according to the invention using carbonic anhydrase, the carbonate or hydrogen carbonate can be dispensed with as the blood serum naturally contains them. In yet other preferential conditions for the implementation of the invention, for example to accelerate lysis, the multifunctional reagent for erythrocytes moreover contains a carbonate or a hydrogen carbonate.

Sodium or potassium carbonate or hydrogen carbonate can for example be mentioned.

In a multifunctional reagent according to the invention, the carbonate or the hydrogen carbonate can be present up to the molar concentration of 0.1 M, particularly up to 0.01 M, and very particularly up to 0.005 M. In very preferential conditions for the implementation of the multifunctional reagent described above, a concentration of 0.0025 M is used.

The concentrations of the compound concerned in the reaction medium (multifunctional reagent+blood sample) for erythrocytic lysis are preferably 0.0001 to 0.1 M, particularly 0.001 to 0.01 M and very particularly 0001 to 0.005 M.

In yet other preferential conditions for the implementation of the invention, the multifunctional reagent for erythrocytes moreover contains a protective agent against the deterioration of the leucocytes such as a fixation agent, in particular an aliphatic aldehyde such as in $C_1$-$C_5$, for example paraformaldehyde and particularly formaldehyde.

The aliphatic aldehyde can be present in a concentration of 0.01% to 5%, particularly 0.04% to 1% and very particularly 0.1% to 0.5%.

In yet more preferential conditions for the implementation of the invention, the multifunctional reagent of the invention also comprises an effective quantity of an anticoagulant agent.

Heparin, in particular ion citrate, EGTA and particularly EDTA can for example be mentioned as anticoagulant agent.

The pH of the mixture without buffer at neutral pH during and after lysis tends to increase, thus provoking cell degradation. The use of a buffer of approximately neutral pH is therefore desirable. Despite the fact that the buffer tends to inhibit lysis, a small quantity of buffer (for example 1-20 mM) can be used thanks to the accelerating effect of a catalyst such as carbonic anhydrase. The use of a carbamate according to the invention allows the use of a buffer of approximately neutral pH.

This is why, in other preferential conditions for the implementation of the invention, the multifunctional reagent of the invention also comprises an effective quantity of a buffer agent particularly pH 6.5 to 7.5. There can for example be mentioned as buffer agent MES (2-(N-morpholino)ethane sulphonic acid), in particular MOPS (3-(N-morpholino)propane sulphonic acid) and particularly HEPES (N-(2-hydroxyethyl)piperazine-N'-(2-ethane sulphonic acid)) and particularly the buffer DIPSO pH 7.5.

In a multifunctional reagent according to the invention, the buffer agent can be present in the molar concentration of 0.0001 to 0.050 M, particularly 0.0005 to 0.03 M and very particularly 0.001 to 0.010 M.

In preferential conditions for the creation of the multifunctional reagent described above without fixing agent, 0.17 M of pyrrolidine hydrochloride, 2.5 mM of potassium hydrogen carbonate, 3 mM of DIPSO buffer pH 7.5, 10 mg/l of carbonic anhydrase and 0.1 mM of EDTA are used.

In very preferential conditions for the creation of the multifunctional reagent described above with fixing agent, 0.3% of formaldehyde is also used.

As seen above, the catalyst agent of the reaction

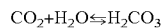

or

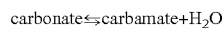

such as carbonic anhydrase, induces the formation by the erythrocytes, from carbonate or from an amine base, of a carbamate combined with the absorption of $CO_2$ by said erythrocytes. The carbamates of the nitrogenated heterocycles can also be used directly to produce lysis of the erythrocytes. Some of these are new products.

This is why a subject of the present application is also a carbamate chosen from
pyrrolidine carbamate,
piperidine carbamate.

The reagents which are the subject of the present invention possess very advantageous properties. They are endowed in particular with remarkable properties which are lyitic with regard to erythrocytes.

These properties are illustrated below in the experimental part. They justify the use of the reagents described above, in a method or a process for lysis or sphering of erythrocytes. Lysis of the red blood cells allows the analysis and/or triage using a flow cytometer of the leucocytes and their subpopulations, platelets, red blood cell residues after lysis, or any other cellular or suspended, element added or not, such as for example spherules.

They also justify the use of the reagents described above, in a process for the preparation of leucocytes.

A subject of the present application is also therefore a method of lysis of the erythrocytes in which a sample of whole blood treated with a anti-coagulant such as EDTA, EGTA, heparin or the citrate ions, is subjected to the action of a lysis reagent described above, to produce at least 95% lysis of the erythrocytes in less than 30 minutes.

It is possible to operate in the absence or in the presence of monoclonal antibodies in order to carry out the labelling of the leucocytic cells. These antibodies can be bound or not bound to a fluorescent compound such as those described below. In preferential conditions of implementation, these antibodies are bound to a fluorescent compound.

The multifunctional reagents described above can be used as follows:

A sample of 0.1 ml of blood treated with an anticoagulant, and incubated beforehand with a monoclonal antibody or a monoclonal antibody combined with a fluorescence marker, or a mixture of monoclonal antibodies combined with fluorescence markers is brought into contact with 2 ml of multifunctional reagent above and left for ten minutes during which the lysis finishes. Such markers are for example CD45-FITC (CD45 combined with fluoresceine isothiocyanate) or CD14 combined with phycoerythrin and are marketed for example by the companies DAKO, BECTON and DICKINSON or BECKMAN COULTER. A reading in a cytometer for example of BECTON and DICKINSON Facscan or BECKMAN COULTER XL type is then carried out either immediately, or up to 3 days after lysis.

In preferential conditions for the implementation of the method of lysis according to the invention, the preferential conditions described above for the multifunctional reagent are chosen.

The systems of lysis covered by the invention can also be used in the presence of a permeation agent such as an aliphatic alcohol or a detergent. A permeation reagent allowing an intracellular immunolabelling including a catalyst such as carbonic anhydrase or a carbamate is also part of the invention. Such a lysis and permeation stage can be carried out optionally after fixation by an aliphatic aldehyde.

In preferential conditions for the implementation of the process described above, a sample of whole blood is brought into contact with a reagent above sufficient to produce the lysis of at least 95% of the erythrocytes in less than 10 minutes.

In other preferential conditions for the implementation of the process described above, the pH of the mixture of the reagent and the sample is between 4 and 9.

But the multifunctional reagent according to the invention also allows the production of the simple sphering of the erythrocytes.

This is why a subject of the present application is also a process of sphering (swelling) of the erythrocytes characterized in that a sample of whole blood treated with an anticoagulant is brought into contact with a quantity of a reagent above sufficient to provoke the sphering of the erythrocytes in such a way as to allow their analysis by an automatic counting device.

In preferential conditions for the sphering of the erythrocytes a sample of blood is brought into contact with a quantity of sphering reagent sufficient to produce sphering in 10 second to 400 second intervals. To avoid lysis of the erythrocytes in a time interval and to control the speed of the sphering, the multifunctional reagent according to the invention can be diluted in a preferably isotonic solution. Between 0 and 10 times the same volume of diluent, preferably between 0.5 and 5 times and particularly between 1 and 3 times can for example be added. In particularly preferential conditions, the choice of isotonic solution is IsoFlow® from Beckman Coulter which contains NaCl: 7.92 g/l, KCl: 0.4 g/l, $NaH_2PO_4$: 0.19 g/l, $Na_2HPO_4$: 1.95 g/l, EDTA: 0.38 g/l, 2-phenoxyethanol: 3 g/l, and NaF: 0.3 g/l.

In other preferential conditions, one or more adjuvants such as fixation reagents, colorants of nucleic acids, and/or isosphering agents such as maltoside (D. H. Tycko, U.S. Pat. No. 5,194,909) are added to the sphering reagent.

As has been seen above, the multifunctional reagent of the invention is not aggressive for the leucocytes and can therefore be used with a view to their preparation. The lysis systems covered by the invention are therefore also tools for the preparation of viable leucocytic cells and can replace the technique of cell separation on Ficoll-Hypaque. The preparation of the viable cells after lysis of blood, pathological blood, bone marrow and any other body fluid, has an application for example for the purposes of research for functional cellular tests, freezing and storage of the cells, etc. As far as the control of cellular viability is concerned, the lysis methods can be used with viability colorants such as eosin, blue tryptan, 7-AAD, LDS 751 etc. Finally, as the lysis according to the studies of the Applicant is a function of the capacity of the erythrocytes to absorb $CO_2$, the system of lysis can be used as a functional parameter of the erythrocytes.

This is why a subject of the present application is also a process for the preparation of leucocytes characterized in that it comprises a stage of lysis of the erythrocytes using a multifunctional reagent such as described above.

The preferential conditions for the implementation of the processes described above also apply to the other subjects of the invention referred to above.

FIG. 1 represents a size-structure diffusion diagram of a blood sample analysed using flow cytometry (BECKMAN COULTER XL) after lysis according to Example 5. Region A corresponds to the lymphocytes, region B corresponds to the monocytes and region C to the granulocytes.

Figure 2A:
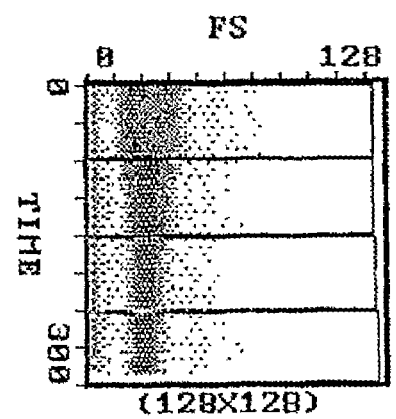
Figure 2D:
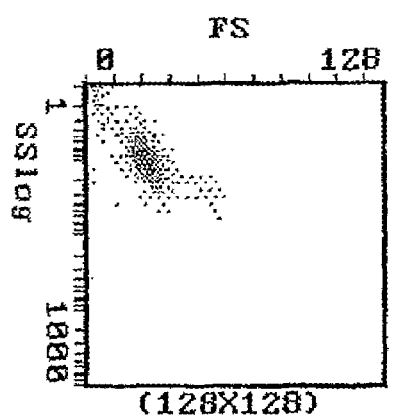
Figure 2B:
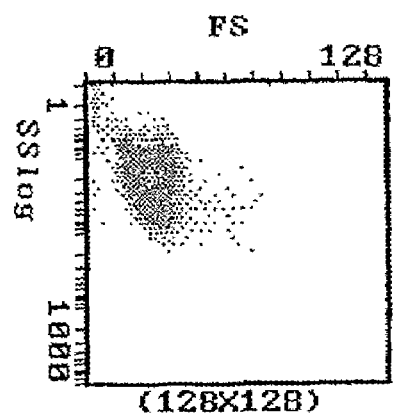
Figure 2E:
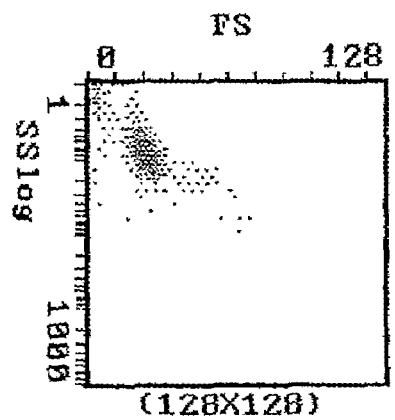
Figure 2C:
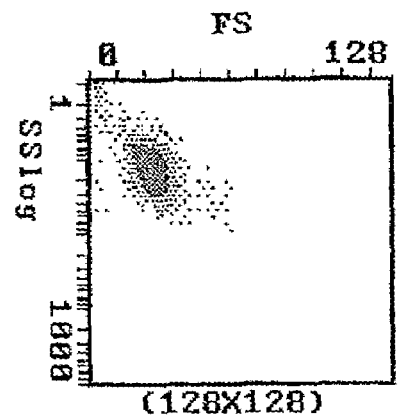

FIGS. 2A-2E represent size-structure diffusion diagrams of a blood sample analysed using flow cytometry (BECKMAN COULTER XL), after sphering according to Example 6. After contact of the erythrocytes with the sphering agent, described in Example 6, the size-structure occurrences of the erythrocytes are represented in 4 intervals of 100 seconds. (FIG. 2A). The sphering and the homogenization of the erythrocytes which results from this over time are illustrated in the size-structure diagrams; FIG. 2B, after 100 seconds; FIG. 2C, after 200 seconds; FIG. 2D, after 300 seconds; FIG. 2E, after 400 seconds.

The following examples illustrate the present application.

EXAMPLE 1

A multifunctional reagent for erythrocytes having the following composition was prepared:

| | |
|---|---|
| Pyrrolidine chloride | 170 mM |
| Potassium hydrogen carbonate | 2.5 mM |
| DIPSO buffer pH 7.5 | 3 mM |
| Bovine carbonic anhydrase (SIGMA) (50000 W-A units) | 10 mg/l |
| EDTA | 0.1 mM |
| pH 7.3 | |

EXAMPLE 2

A multifunctional reagent for erythrocytes having the following composition was prepared:

| | |
|---|---|
| Pyrrolidine chloride | 170 mM |
| Potassium hydrogen carbonate | 2.5 mM |
| DIPSO buffer pH 7.5 | 3 mM |
| Bovine carbonic anhydrase (SIGMA) (50000 W-A units) | 10 mg/l |
| EDTA | 0.1 mM |
| Formaldehyde | 0.1% |
| pH 7.3 | |

EXAMPLE 3

A multifunctional reagent for erythrocytes having the following composition is prepared:

| | |
|---|---|
| Piperidine chloride | 170 mM |
| Potassium hydrogen carbonate | 2.5 mM |
| DIPSO buffer pH 7.5 | 3 mM |
| Bovine carbonic anhydrase (SIGMA) (50000 W-A units) | 10 mg/l |
| EDTA | 0.1 mM |
| pH 7.3 | |

EXAMPLE 4

A multifunctional reagent for erythrocytes having the following composition was prepared:

| | |
|---|---|
| Ammonium chloride | 155 mM |
| Potassium hydrogen carbonate | 2.5 mM |

-continued

| | |
|---|---|
| DIPSO buffer pH 7.5 | 3 mM |
| Bovine carbonic anhydrase (SIGMA) (50000 W-A units) | 10 mg/l |
| EDTA | 0.1 mM |
| pH 7.3 | |

EXAMPLE 5

Performance of a Lysis

100 μl of whole blood is mixed with 1 ml of a lysis agent of Example 1. The solution is left to rest at ambient temperature for 10 minutes and the leucocytes are counted by cytometry.

EXAMPLES 6 to 8

Preparation of Pyrrolidine Piperidine and Morpholine Carbamates

A mixture of sodium bicarbonate and a quantity of each compound (molar ratio 1:2), was heated to 100° C. accompanied by stirring. The reaction is characterized by a solidification of the mixture, which occurs after approximately an hour. The sought carbamates were recovered after extraction with methanol. The molecular structure of these synthesized compounds was verified by NMR spectrometry $^{13}$C at 200 MHz.

These analyses (in deuterated methanol) made it possible to obtain the following chemical shifts (δ: ppm):
1/Pyrrolidine carbamate: 26.44; 27.24; 47.32; 47.63 ($CH_2$; 165.02 (C=O)
2/Piperidine carbamate: 25.69; 26.58; 27.39; 28.71; 47.65 ($CH_2$; 162.76 (C=O)
3/Morpholine carbamate: 47.14; 68.42 ($CH_2$; 162.81 (C=O)

EXAMPLE 9

Preparation of a Sphering Agent

A sphering agent was prepared by mixing 2 volumes of reagent according to Example 1 and a volume of Isoflow®, an isotonic composition marketed by BECKMAN COULTER.

EXAMPLE 10

Cytometry After Sphering

A volume of blood of 4 microliters was placed in contact with 1 ml of the sphering agent of Example 9. The process of sphering was tracked by cytometry as a function of time in a BECKMAN COULTER XL cytometer. The results are presented in FIGS. 2A-2E mentioned above.

Experiment 1

The speed of lysis by the ammonium ion and by nitrogenated heterocycles in the presence of $KHCO_3$ (10 mM) or in the presence of their respective carbamate derivatives (0.4 mM) was studied. A volume of 2 ml of reagent was used for a volume of 0.1 ml of whole blood treated with anticoagulant (EDTA). Variations in pH were obtained by adding a 1 M aqueous solution of HCl before the addition of carbamate. The carbamates (100 mM in methanol) were added to the mixtures at the start of the reaction. The pH of the reaction mixture was measured. The lysis process was tracked spectrophotometrically (measurement of optical density at 700 nm). The lysis time is determined by the time necessary to obtain a minimum level.

The results obtained are the following:

| | Time necessary to reach total lysis (maximum transparency) | pH during the lysis reaction |
|---|---|---|
| $NH_4Cl$ (150 mM), $KHCO_3$ (10 mM) | 7 mn | 7.40 |
| Idem | 4 mn | 7.03 |
| $NH_4Cl$ (150 mM) ammonium carbamate (0.4 mM) | 1 mn 50 | 7.20 |
| Pyrrolidine (150 mM), $KHCO_3$ (10 mM) | 7 mn | 7.20 |
| Idem | 6 mn | 7.75 |
| Pyrrolidine, pyrrolidine carbamate (0.4 mM) | 3 mn | 7.66 |
| Piperidine (150 mM), $KHCO_3$ | 15 mn | 7.30 |
| Idem | 10 mn | 7.8 |
| Piperidine (150 mM), piperidine carbamate (0.4 mM) | 6 mn 40 | 7.68 |
| Morpholine (150 mM), $KHCO_3$ (10 mM) | 12 mn | 6.82 |
| Morpholine (150 mM), morpholine carbamate (0.4 mM) | 8 mn | 6.90 |

Conclusion: It will be seen that the addition of the different carbamates to the ammonium ion and to the nitrogenated heterocycles induces a much greater speed of lysis than that obtained by adding hydrogen carbonate at a concentration 25 times that of the carbamate. As the table shows, the lytic effect of the carbamates does not depend on the pH.

Experiment 2. Demonstration of the catalyst role of carbonic anhydrase in the reaction carbonate⇌carbamate+H2O;

The reaction $(NH_4)_2CO_3 \leftrightarrows NH_2CO_2NH_4+H_2O$ was studied through the conversion of the ammonium carbamate into ammonium carbonate measured by their difference in solubility in an aqueous solution of 85% of acetone in which the carbonate precipitates and not the carbamate.

| Reaction mixture | Duration before complete precipitation in 85% of acetone |
|---|---|
| 100 mM $NH_2CO_2NH_4$ | 240 min |
| 100 mM $NH_2CO_2NH_4$ + 0.001 mg/ml of carbonic anhydrase | 10 min |

Conclusion.: The results show that the carbonic anhydrase, in addition to catalysing the conversion $CO_2+H_2O \leftrightarrows H_2CO_3$ as is well known, also catalyses the conversion carbonate⇌carbamate+$H_2O$ Experiment 3: Demonstration of the effect on the speed of lysis of carbonic anhydrases originating from different sources.

In a lysis reagent according to Example 1, the component carbonic anhydrase at 50,000 W-A U/l was replaced by preparations of carbonic anhydrase as indicated in the table, each at 5000 W-A U/l. The lysis process was tracked spectrophotometrically (measurement of the OD at 700 nm). The duration of the lysis is determined by the time necessary to achieve a minimum level.

| Supplier | Reference | Origin | Speed of lysis at 5000 W-A U/l |
| --- | --- | --- | --- |
| Control | without enzyme | | 15.00 min |
| Sigma | C-3934 | Bovine | 7.30 min |
| Biozyme | CABI | Bovine | 7.06 min |
| Biozyme | CABII | Bovine | 8.30 min |
| Sigma | CAII, C-2522 | Bovine | 8.51 min |
| Sigma | CAII, C-6165 | Human | 7.06 min |
| Sigma | CAI, C-4396 | Human | 5.06 min |
| Sigma | CAI, C-5290 | Human | 3.24 min |
| Sigma | CAI, C-1266 | Rabbit | 8.00 min |

Conclusion. The different preparations of carbonic anhydrase all increase the speed of lysis.

The invention claimed is:

1. A lysis reagent for blood cell analysis comprising;
   (a) an enzyme consisting essentially of a carbonic anhydrase in an amount sufficient to enable lysis of erythrocytes of a blood sample;
   (b) a carbonate or hydrogen carbonate salt; and
   (c) an ammonium salt or a heterocyclic amine or salt thereof; said heterocyclic amine being monocyclic with a 5 to 6 member ring;
   wherein said carbonic anhydrase has a concentration from 0.002 mg to 200 mg per liter, equivalent to from 10 to $10^6$ Wilbur-Anderson units uer liter (W-A U/liter).

2. The lysis reagent of claim 1, wherein said carbonic anhydrase comprises carbonic anhydrase I or carbonic anhydrase II.

3. The lysis reagent of claim 1, wherein said ammonium salt or said heterocyclic amine or salt thereof has a concentration from 10 to 250 mM.

4. The lysis reagent of claim 1, wherein said ammonium salt comprises ammonium halide.

5. The lysis reagent of claim 1, wherein said heterocyclic amine comprises pyrazolidine, imidazolidine, imidazoline, piperazine, morpholine, piperidine, or pyrrolidine.

6. The lysis reagent of claim 1, wherein said carbonate or hydrogen carbonate salt has a concentration from 1 to 100 mM.

7. The lysis reagent of claim 1, wherein said reagent has a pH in a range from 4 to 9.

8. The lysis reagent of claim 1 further comprising a buffer in a concentration range from 0.1 to 50 mM.

9. The lysis reagent of claim 8, wherein said buffer comprises 2-(N-morpholino)ethane sulphonic acid (MES), 3-(N-morpholino)propane sulphonic acid (MOPS), N-(2-hydroxyethyl)piperazine-N'-(2-ethane sulphonic acid) (HEPES), or 3-[N,N-bis(2-Hydroxyethyl)amino]-2-hydroxypropanesulfonic acid (DIPSO).

10. The lysis reagent of claim 1 further comprising an anticoagulant agent comprising heparin, EGTA, citrate, or EDTA.

11. The lysis reagent of claim 1 further comprising a fixation agent comprising formaldehyde, or paraformaldehyde.

12. A lysis reagent for blood cell analysis comprising:
   (a) an enzyme consisting essentially of a carbonic anhydrase in a concentration from 0.002 mg to 200 mg per liter, equivalent to from 10 to $10^6$ (W-A U/liter), to enable lysis of erythrocytes of a blood sample;
   (b) a carbonate or hydrogen carbonate salt in a concentration from 1 to 100 mM; and
   (c) an ammonium salt or a heterocyclic amine or salt thereof; in a concentration from 10 to 250 mM; said heterocyclic amine being monocyclic with a 5 to 6 member ring.

13. The lysis reagent of claim 12, wherein said carbonic anhydrase has a concentration from 0.02 mg to 20 mg per liter, equivalent to from $10^2$ to $10^5$ (W-A U/liter).

14. The lysis reagent of claim 12, wherein said carbonic anhydrase comprises carbonic anhydrase I or carbonic anhydrase II.

15. The lysis reagent of claim 12, wherein said ammonium salt or said heterocyclic amine or salt thereof has a concentration from 80 to 250 mM.

16. The lysis reagent of claim 12, wherein said ammonium salt comprises ammonium halide.

17. The lysis reagent of claim 12, wherein said heterocyclic amine comprises pyrazolidine, imidazolidine, imidazoline, piperazine, morpholine, piperidine, or pyrrolidine.

18. The lysis reagent of claim 12, wherein said reagent has a pH in a range from 4 to 9.

19. The lysis reagent of claim 12 further comprising a buffer in a concentration range from 0.5 to 30 mM.

20. The lysis reagent of claim 19, wherein said buffer comprises 2-(N-morpholino)ethane sulphonic acid (MES), 3-(N-morpholino)propane sulphonic acid (MOPS), N-(2-hydroxyethyl)piperazine-N'-(2-ethane sulphonic acid) (HEPES), or 3-[N,N-bis(2-Hydroxyethyl)amino]-2-hydroxypropanesulfonic acid (DIPSO).

21. The lysis reagent of claim 12 further comprising an anticoagulant agent comprising heparin, EGTA, citrate, or EDTA.

22. The lysis reagent of claim 12 further comprising a fixation agent comprising formaldehyde, or paraformaldehyde.

23. The lysis reagent of claim 20, wherein said formaldehyde, or paraformaldehyde has a concentration from 0.01% to 1%.

24. A lysis reagent for blood cell analysis comprising:
   (a) an enzyme consisting essentially of a carbonic anhydrase in a concentration from 0.002 mg to 200 mg per liter, equivalent to from 10 to $10^6$ (W-A U/liter), to enable lysis of erythrocytes of a blood sample;
   (b) a carbonate or hydrogen carbonate salt in a concentration from 1 to 100 mM; and
   (c) ammonium chloride, morpholine chloride, pyrrolidine chloride, or piperidine chloride in a concentration from 10 to 250 mM; and
   (d) a buffer in a concentration from 0.5 to 30 mM.

25. A lysis reagent for blood cell analysis comprising:
   (a) an enzyme consisting essentially of carbonic anhydrase in an amount sufficient to enable lysis of erythrocytes of a blood sample; and
   (b) an ammonium salt or a heterocyclic amine or salt thereof;
   wherein said carbonic anhydrase has a concentration from 0.002 mg to 200 mg per liter, equivalent to from 10 to $10^6$ (W-A U/liter).

26. The lysis reagent of claim 25, wherein said ammonium salt or said heterocyclic amine or salt thereof has a concentration from 10 to 250 mM.

27. The lysis reagent of claim 25, wherein said heterocyclic amine comprises pyrazolidine, imidazolidine, imidazoline, piperazine, morpholine, piperidine, or pyrrolidine.

28. The lysis reagent of claim 25, wherein said reagent has a pH in a range from 4 to 9.

* * * * *